(12) United States Patent
Kopperschmidt

(10) Patent No.: US 12,702,741 B2
(45) Date of Patent: Aug. 11, 2026

(54) METHOD FOR ASSESSING A MEASURED PRESSURE VALUE, AND APPARATUSES

(71) Applicant: Fresenius Medical Care Deutschland GmbH, Bad Homburg (DE)

(72) Inventor: Pascal Kopperschmidt, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 534 days.

(21) Appl. No.: 18/547,419

(22) PCT Filed: Feb. 23, 2022

(86) PCT No.: PCT/EP2022/054506
§ 371 (c)(1),
(2) Date: Aug. 22, 2023

(87) PCT Pub. No.: WO2022/180086
PCT Pub. Date: Sep. 1, 2022

(65) Prior Publication Data

US 2024/0139396 A1 May 2, 2024

(30) Foreign Application Priority Data

Feb. 26, 2021 (DE) ......................... 102021104683.1

(51) Int. Cl.
*A61M 1/36* (2006.01)

(52) U.S. Cl.
CPC ........ *A61M 1/3639* (2013.01); *A61M 1/3656* (2014.02); *A61M 2205/18* (2013.01); *A61M 2205/3331* (2013.01); *A61M 2205/50* (2013.01)

(58) Field of Classification Search
CPC .............. A61M 1/3639; A61M 1/3656; A61M 2205/18; A61M 2205/3331;
(Continued)

(56) References Cited

U.S. PATENT DOCUMENTS 9,289,544 B2 * 3/2016 Olde ................... A61M 1/3656
2012/0330214 A1 12/2012 Peters et al.
(Continued)

FOREIGN PATENT DOCUMENTS

DE 102009060668 6/2011
JP 2017-205490 A 11/2017
WO WO 2015/003795 1/2015

OTHER PUBLICATIONS

International Search Report and Written Opinion in International Appln. No. PCT/EP2022/054506, mailed Jun. 9, 2022, 18 pages (with English translation).
(Continued)

*Primary Examiner* — Adam Marcetich
*Assistant Examiner* — Brandon W. Levy
(74) *Attorney, Agent, or Firm* — Fish & Richardson P.C.

(57) ABSTRACT

The present disclosure relates to a method for assessing a measured pressure value, with the provision of a blood treatment apparatus, connectable to a blood tubing set which includes an arterial blood line and a venous blood line, wherein the blood treatment apparatus further includes a blood pump, pressure meter for measuring the pressure in the blood lines, in each case with the determination of at least one pressure measurement value, an alarm output device for outputting an alarm based on the pressure measurement value and a control device for controlling or regulating the blood pump. The method includes providing an alarm criterion memory for defining an alarm event and providing a reference data memory. The method encompasses measuring the prevailing pressures, assessing the determined pressure measurement values using alarm criteria, and repeating the pressure measuring processes at certain conveying rates of the blood pump to assess whether it is a false alarm.

17 Claims, 5 Drawing Sheets

(58) Field of Classification Search
CPC .......... A61M 2205/50; A61M 2205/52; A61M 1/1603; A61M 1/267; A61M 2205/3334; A61M 2205/3344; A61M 1/14
See application file for complete search history.

(56) References Cited

U.S. PATENT DOCUMENTS

| | | | | |
|---|---|---|---|---|
| 2016/0158433 | A1 | 6/2016 | Wiktor et al. | |
| 2017/0100142 | A1* | 4/2017 | Look | A61B 17/22 |
| 2017/0296736 | A1* | 10/2017 | Golarits | G16H 20/40 |
| 2018/0036470 | A1 | 2/2018 | Hasegawa et al. | |
| 2018/0303999 | A1* | 10/2018 | Thys | A61M 1/3639 |

OTHER PUBLICATIONS

Sukhova, "Alarm Fatigue. Medical Device Interoperability for Quiet ICU," Dec. 17, 2020, retrieved from URL <https://auriga.com/blog/2020/alarm-fatigue/>, 5 pages.

* cited by examiner

METHOD FOR ASSESSING A MEASURED PRESSURE VALUE, AND APPARATUSES

CROSS-REFERENCE TO RELATED APPLICATIONS

The present application is the national stage entry of International Application No. PCT/EP2022/054506, filed on Feb. 23, 2022, and claims priority to Application No. 102021104683.1, filed in the Federal Republic of Germany on Feb. 26, 2021, the disclosures of which are expressly incorporated herein in their entirety by reference thereto.

TECHNICAL FIELD

The present disclosure relates to a method as described herein, a control device as described herein, a blood treatment apparatus as described herein, a digital storage medium as described herein, a computer program product as described herein, and a computer program as described herein.

BACKGROUND

Alarms, in particular pressure alarms, are regularly issued when a pressure measurement value obtained by measuring pressure—e.g., in the extracorporeal blood circuit during a blood treatment session of a patient carried out using a blood treatment apparatus, for example hemodialysis—deviates from a stored reference pressure value, exceeds the stored reference pressure value, falls short of the stored reference pressure value, and so forth.

These alarms are accompanied by an alarm signal, in particular an audible and/or visual alarm signal, for the caregiver of the patient being treated and/or can also lead to a, usually temporary, interruption of the treatment session.

In conventional blood treatment apparatuses, for example, the pressures in the blood lines between the blood treatment apparatus and the patient's vascular access are monitored.

If an alarm is triggered, the user is requested to rectify the cause of the alarm, confirm that the alarm has been acknowledged and, if applicable, initiate the continuation of the treatment.

In clinical practice, these measures require a high level of effort on the part of the personnel in the event of an alarm and pose a hygiene risk of possible cross-contamination among patients and/or personnel.

Frequently, the pressure fluctuations that lead to alarms are not critical, since they are caused either by a momentary kinking of the blood circuit (alternatively: blood tubing set) or by repositioning or movements of the patient or therapy-related, hemodynamic fluctuations.

Therefore, one task of the present disclosure may be to propose a method for assessing a measured pressure value. Furthermore, suitable devices are to be specified.

SUMMARY

The task according to the present disclosure can be achieved by the method as described herein. It can further be achieved by the control device as described herein, the blood treatment apparatus as described herein, the digital storage medium as described herein, the computer program product as described herein, and the computer program as described herein.

Thus, according to the present disclosure, a method for assessing a measured pressure value is proposed.

The method runs on or includes providing a blood treatment apparatus which is connectable to a blood tubing set of an extracorporeal blood circuit. Such a blood tubing set includes an arterial blood line and a venous blood line.

The blood treatment apparatus provided or to be provided includes a blood pump by which, in use or as intended, blood is conveyed extracorporeally along the arterial blood line. The blood treatment apparatus further includes a pressure meter or sensor for measuring the pressure in the arterial blood line and/or a pressure meter or sensor for measuring the pressure in the venous blood line. According to the intended use, they serve for measuring at least one pressure measurement value prevailing and/or determined in the arterial blood line or in the venous blood line.

Furthermore, an alarm output device for outputting an alarm or pressure alarm based on the determined pressure measurement value or its level, preferably when an alarm event is present, is included within the blood treatment apparatus or is connected to it or its pressure meters. Further, the blood treatment apparatus includes a control device for controlling or regulating the blood pump and possibly further components of the blood treatment apparatus.

The method further encompasses providing an alarm criterion memory for storing at least one predetermined alarm criterion which defines an alarm event, or the use thereof.

The alarm criterion memory can be stored in the sensor, alternatively in an assessment device, in the control device, it can be part of the programming, etc. The at least one alarm criterion can have been determined and saved in advance. Alarm criteria can in particular be or encompass threshold values, ranges of fluctuation in the measured pressure, the occurrence of pressure fluctuations over time, the occurrence of pressure patterns, etc.

The method further encompasses providing, or using, a reference data memory which includes at least one data set or record, which in turn may include one or more reference pressure profiles, reference pressure ranges, or reference pressure values. The reference data memory may optionally be part of the blood treatment apparatus. The memory device may be or include any embodiment of a memory device set forth herein.

The method described herein further includes the following features a) to f), referred to herein as assessment features, some of which are optional:

a) measuring the prevailing pressure in the arterial and/or in the venous blood line at an initial conveying rate (such as the treatment conveying rate set for the current treatment of the patient) of the blood pump by the corresponding arterial or venous pressure meter, respectively, thereby determining a pressure measurement value. A measured pressure measurement value (e.g., in the unit mm/Hg, mbar, or the like) can, for example, be a pressure measured directly in the corresponding line, or alternatively, the result of a determination of this pressure via auxiliary measurements or observations, conversions, and the like.

b) Assessing the pressure measurement value thus obtained on the basis of the alarm criterion stored in the alarm criterion memory. As already discussed above, the alarm criterion can be or include, for example, exceeding or falling below a threshold value and/or leaving a threshold range. It can depend on technical parameters such as the applied conveying rate of a pump or the like. The assessment includes determining whether the pressure measurement value meets the alarm criterion or satisfies an alarm criterion, so that there is an alarm event. If it does not satisfy the alarm criterion, or if it does not meet it, there is no alarm event—at least measured against the alarm criterion on which it is based.

c) Controlling the blood pump in such a way that it conveys along the arterial blood line at one or more conveying rates referred to herein as reference conveying rates or that it provides the required output. According to the present disclosure, however, this controlling or activating of the blood pump only takes place in the event that the pressure measurement value satisfies the alarm criterion. The reference conveying rate, or at least one of the reference conveying rates, is lower than the initial conveying rate. After a positive determination that the pressure measurement value meets the alarm criterion and thus an alarm event is present, the blood pump is controlled in order to convey at a lower conveying rate, which is referred to herein as the reference conveying rate, than before.

d) Measuring the pressure prevailing in the arterial and/or venous blood line at the one or more reference conveying rates of the blood pump by the corresponding pressure meter. In this case, at least one pressure measurement value, referred to herein as an assessment pressure measurement value, is determined. Optionally, one or more arterial and/or one or more venous assessment pressure measurement values can be recorded. The assessment pressure measurement value(s) can, after the application of mathematical methods, represent one or more profiles or be or encompass one or more reference pressure profiles.

e) Evaluating the at least one assessment pressure measurement value using, or via comparison with, the data set(s) stored in the reference data memory, with at least one evaluation result being determined. The evaluation can be a signal, for example.

f) Outputting an alarm via the alarm output device only in the event that the evaluation result satisfies predetermined requirements for outputting an alarm.

In order to output an alarm, both the alarm criterion (see above) and the evaluation result (see features e) and f)) must indicate that an alarm event has occurred.

In some embodiments, the outputting of an alarm can be or encompass the outputting of a message which, in particular, refers to the evaluation result.

The present disclosure also relates to a control device. The control device is configured to execute or initiate the assessment features of the method according to the present disclosure and/or further features as disclosed herein in any combination, in interaction with a provided blood treatment apparatus, an alarm criterion memory, and a reference data memory.

The blood treatment apparatus, which is connected to a blood tubing set which includes an arterial blood line and a venous blood line, further includes a blood pump for conveying blood extracorporeally along the arterial blood line. The blood treatment apparatus further includes a pressure meter for measuring pressure in the arterial blood line and/or a pressure meter for measuring pressure in the venous blood line, respectively, to determine at least one arterial or venous pressure measurement value.

The alarm output device is used to output an alarm or pressure alarm based on the pressure measurement value or its level in the event of an alarm. The control device is used to control or regulate the blood pump.

The alarm criterion memory is suitable and/or provided for storing and/or has stored at least one predetermined alarm criterion which defines an alarm event. The alarm criterion may be defined by the manufacturer, by the service technician, by the treating physician, and/or has preferably been defined or stored prior to the start of the treatment session.

The reference data memory contains at least one data set including one or more reference pressure profiles, reference pressure ranges, or reference pressure values. The reference data can be or are stored in tabular form and/or as a functional approximation (for example, using tools such as Splinefit, Polynomfit, etc.).

An interaction may be or include actuation, control, or regulation. An interaction may be or require a signal connection.

Where reference is made herein to a signal connection or communication connection between two elements, components, etc., this may be understood to mean a connection that exists in use. Likewise, it may be understood herein that there is preparation for such a signal connection (wired, wireless, or otherwise implemented), for example, by coupling the two components, such as by pairing, etc.

Pairing is a process that occurs in the context of computer networks to establish an initial link between computer units for the purpose of communication. The best-known example of this is the establishment of a Bluetooth connection, via which various devices (e.g., smartphone, headphones) are connected to each other. Pairing is sometimes also referred to as bonding.

Further, the present disclosure relates to a blood treatment apparatus.

The blood treatment apparatus according to the present disclosure includes a blood pump for extracorporeally conveying blood along the arterial blood line.

Further, the blood treatment apparatus includes a pressure meter for measuring the pressure in the arterial blood line and/or a pressure meter for measuring the pressure in the venous blood line, which are each suitable and/or provided for determining at least one pressure measurement value arterial or venous, respectively.

Further, the blood treatment apparatus includes an alarm output device. The alarm output device is for outputting an alarm or pressure alarm based on the pressure measurement value or its level in an alarm event. Depending on the embodiment, the alarm may be audible, for example via a beep, visual, for example via a flashing light or a message, and/or haptic, for example via vibration, or output via other means.

The blood treatment apparatus further includes an alarm criterion memory for storing at least one predetermined alarm criterion. The alarm criterion is provided to define an alarm event, as set forth herein.

Further, the blood treatment apparatus includes a reference data memory. This includes at least one data set including or consisting of one or more reference pressure profiles, reference pressure ranges, and/or reference pressure values.

The blood treatment apparatus further includes a control device as described herein.

Alternatively, the blood treatment apparatus is connected to the aforementioned devices, respectively.

A digital, particularly non-volatile storage medium, as described herein, particularly in the form of a machine readable carrier, particularly in the form of a diskette, memory card, CD, DVD EPROM, FRAM (Ferroelectric RAM) or SSD (Solid-State-Drive), or NOVRAM, particularly with electronically or optically readable control signals, can be configured so that a conventional control device is configured to be a control device as described herein, with which the features, in particular the assessment features, of the method described herein can be initiated.

In this, all, some or several of the features, in particular the assessment features, can be initiated.

A computer program product as described herein includes a volatile or transient program code or one stored on a machine readable carrier or a signal wave, via which a conventional control device may be configured into a control device described herein, with which the features, in particular the assessment features, of the method described herein may initiated.

In doing so, all, some or several of the features of this method, especially the assessment features, can be initiated.

A computer program product, for example, can be understood as described herein as a computer program stored on a carrier, an embedded system being a comprehensive system with a computer program (e.g., electronic device with a computer program), a network of computer implemented computer programs (e.g., client/server-system, cloud computing system etc.), or a computer on which a computer program is loaded, runs, is stored, is executed or developed.

The term "machine readable carrier" as is as used herein, refers in certain embodiments of the present disclosure to a carrier, which contains data or information interpretable by software and/or hardware. The carrier may be a data carrier, such as a diskette, a CD, DVD, a USB stick, a flashcard, an SD card, or the like, as well as any other memory or any other storage medium referred to herein.

A computer program disclosed herein includes a program code, via which a conventional control device can be configured into a control device as described herein, with which the features, in particular the assessment features of the method described herein can be initiated, when the computer program runs on a computer.

Thereby, all, some or several of the features of this method, in particular the assessment features can be initiated.

A computer program can, for example be taken to mean a physical, distributable software-product, which includes a program.

An identifying or determining, in particular of data and/or values, may be or encompass investigating an existence or non-existence, obtaining, recording, measuring, evaluating, processing, comparing, estimating, interpreting or estimating, inferring, calculating, achieving, eliciting, attaining, and/or recognizing.

In all of the statements made herein, the use of the expression "may be" or "may have" and so on, is to be understood synonymously with "preferably is" or "preferably has," and so on respectively, and is intended to illustrate an embodiment according to the present disclosure.

Whenever numerical words are mentioned herein, the person skilled in the art shall recognize or understand them as indications of a numerical lower limit. Unless it leads the person skilled in the art to an evident contradiction, the person skilled in the art shall comprehend the specification for example of "one" as encompassing "at least one". This understanding is also equally encompassed by the present disclosure as the interpretation that a numeric word, for example, "one" may alternatively mean "exactly one", wherever this is evidently technically possible for the person skilled in the art. Both understandings are encompassed by the present disclosure and apply herein to all used numerical words.

Whenever the term "programmed" or "configured" is mentioned herein, it is also disclosed that these terms are interchangeable with one another.

Whenever an embodiment is mentioned herein, it represents an exemplary embodiment according to the present disclosure.

When it is disclosed herein that the subject-matter according to the present disclosure includes one or several features in a certain embodiment, it is also respectively disclosed herein that the subject-matter according to the present disclosure does, in other embodiments, likewise according to the present disclosure, explicitly not include this or these features, for example, in the sense of a disclaimer. Therefore, for every embodiment mentioned herein it applies that the converse embodiment, e.g., formulated as negation, is also disclosed.

Embodiments according to the present disclosure may include one or more of the aforementioned and/or following features in any technically possible combination.

In some embodiments, the method described herein includes, as a further assessment feature (or feature which is used to assess), stopping the blood pump if and when the predetermined alarm criterion is met. Such stopping may occur before the blood pump is controlled to convey at the at least one, or a first, reference conveying rate. Alternatively, the method encompasses lowering the conveying rate of the blood pump from the initial conveying rate to a reference conveying rate below the initial conveying rate instead of stopping the conveying rate of the blood pump.

In several embodiments, the method encompasses as a further assessment feature that the alarm output device does not output an alarm when the pressure measurement value satisfies the alarm criterion stored in the alarm criterion memory, but the evaluation result does not meet the predetermined requirements for outputting an alarm.

In this case, no alarm can be issued and the medical staff cannot be informed, at least audibly, visually and/or in any other way that may be perceived as distracting, that pressure measurement values have in the meantime satisfied the alarm criterion. Alternatively, the medical personnel can be informed that pressure measurement values have in the meantime satisfied the alarm criterion. Such an indication can be a message that does not require human intervention (for example, by definition, for example, in the manual).

In some embodiments, the method encompasses, as a further assessment feature, controlling the blood pump in order to initiate it, possibly after a period of time required for it to restart, again using the initial conveying rate or a conveying rate related to it (e.g., 90% of the initial conveying rate) or at a preset resumption rate in the event that the evaluation result does not satisfy the predetermined requirements for issuing an alarm.

In several embodiments, the method encompasses as further assessment features, particularly at the beginning of a treatment session, controlling the blood pump so that it conveys blood along the arterial blood line at one or more reference conveying rates, furthermore a measuring of the pressure prevailing in the arterial and/or venous blood line at the one or more reference conveying rates of the blood pump.

The measuring can be carried out in each case via the corresponding pressure meter in the associated line and serves to determine in each case at least one reference pressure measurement value associated with a reference conveying rate. A profile can be determined or recorded optionally from several measured reference pressure measurement values, in particular a characteristic line.

In these embodiments, storing at least one data set in the reference data memory is also encompassed by the method as an assessment feature, wherein the data set includes the one or more reference pressure measurement value(s), or at least one reference pressure profile generated therefrom.

When reference pressure measurement values are referred to herein, this means values that serve as a reference and are themselves measured. If, on the other hand, reference pressure values are referred to herein, this means values that also serve as a reference but were not necessarily actually measured. Rather, they may be, for example, rounded values, values averaged over several reference measurements, weighted values or values modified, estimated, adjusted, etc. in some other way, which refer directly or indirectly to measured pressure values, but were not collected by a pressure sensor. In certain embodiments, therefore, the terms "reference pressure measurement values" measured on the same or other patients and "reference pressure values" that have already been processed in some way may be used interchangeably.

In several embodiments, the above concept also applies to the term "assessment pressure measurement value". This can be measured and used without needing to be processed in the method described herein. In the sense of the present disclosure, this term "assessment pressure measurement value" refers alternatively to assessment pressure values which are based on measured values but differ from the respective measured measurement results by being processed, e.g., by averaging, smoothing, etc. Thus, interchangeability of the terms "assessment pressure value" and "assessment pressure measurement value" is also encompassed by the present disclosure.

In some embodiments of the method, the assessment feature of the evaluation, by which the evaluation result is obtained, is or encompasses forming a difference between the assessment pressure measurement value measured by the pressure sensor and the one or more reference pressure (measurement) value(s) contained in the data set, where the latter is a written form which encompasses both measured and unmeasured reference pressure values. Alternatively, in several embodiments the difference between the assessment pressure measurement value measured by the pressure sensor and the reference pressure profile(s) created from the reference pressure (measurement) values is calculated.

In some embodiments, the evaluation for obtaining the evaluation result encompasses or consists of smoothing, in particular via a median filter, the pressure profile measured via the first pressure sensor and/or the pressure profile measured via the second pressure sensor.

In several embodiments, the evaluation to obtain the evaluation result may be or consist of forming a differential pressure profile between the reference pressure profile and a pressure profile determined for assessing, based on the assessment pressure measurement values.

In some embodiments, the evaluation to obtain the evaluation result is or consists of integrating the differential pressure profile over time.

In several embodiments, a reference pressure profile is determined from reference pressure measurement values measured by the first pressure sensor and/or by the second pressure sensor while the blood pump is conveying the fluid or is correspondingly controlled in order to convey the fluid.

In some embodiments, pressure sensors are pressure gauges and vice versa.

In several embodiments, the pressure measurement values and/or the reference (measured) pressure value are not pressure amplitudes.

In some embodiments of the blood treatment apparatus described herein, the control device is further configured to issue an alarm via an alarm output device, which may be part of the blood treatment apparatus, to stop a treatment option via the blood treatment apparatus and/or to stop a pump of the blood treatment apparatus, preferably a pump that conveys medical fluid, in particular dialysis fluid. According to the present disclosure, this is done when the control device determines or recognizes that the evaluation result confirms the previously determined alarm event.

In several embodiments, the alarm criterion and/or the reference pressure profiles, reference pressure ranges, or reference intervals may be based on or take into account the set treatment option of the blood treatment apparatus.

In some embodiments, the blood treatment apparatus described herein is configured as a blood purification device or dialysis device, for hemodialysis, hemofiltration, or hemodiafiltration, as a dialysis device in any other embodiment for blood purification known to the person skilled in the art, or as a plasmapheresis device.

In certain embodiments, the blood treatment apparatus is configured for use for continuous venous hemodiafiltration (CVV-HDF) and/or for use for acute dialysis or as a critical care device.

In several embodiments, in addition to comparing assessment pressure measurement values recorded during the current treatment with the reference pressure profile recorded at the beginning of the treatment, the reference pressure profile itself may also be evaluated or processed. For this purpose, for example, the reference pressure profile recorded at the beginning of the treatment (or distinctive points thereof) can be compared with reference pressure profiles or reference pressure values from the patient's history. The reference pressure profiles or reference pressure values from the history can be or encompass values recorded over past treatment(s) of the same patient and/or further patients. This means that incidents can already be detected at the beginning of the treatment session which influence the recorded reference pressure profile. Thus, under certain circumstances, a changed, for example shifted, reference pressure profile could indicate problems in connection with the blood treatment. For example, an incorrectly positioned needle can be detected by such a comparison of the reference pressure profile.

In some embodiments, individual, several or all devices for carrying out the method described herein, in particular the alarm criterion memory and/or the reference data memory, may be implemented in a cloud. In these embodiments, the memory contents are advantageously retrievable from multiple provided blood treatment apparatuses for the purpose of processing, and (alarm) outputs can be made to different terminal devices, e.g., smartphones of the treating personnel.

In certain embodiments, the blood treatment apparatus is connected to an extracorporeal blood circuit and/or a blood tubing set.

In several embodiments, a reference pressure profile is a sequence of at least 3, 5, 30, 50, or more measurements, or a sequence of measurements at 3, 5, 30, 50, or more time points. The time points may be within a time duration of at most 3, 5, 10, 15, 20, or more seconds.

In some embodiments, controlling the blood pump to measure the one or more reference pressure measurement values and storing them is carried out at the beginning of a treatment session.

In several embodiments, the reference pressure measurement values are determined for the pressures prevailing in both the arterial and venous blood lines. The evaluation is performed using, in particular subsequent to a statistical evaluation, the sum and/or the average value of the pressures prevailing in the arterial and venous blood lines. For the evaluation, e.g., by comparison, a corresponding reference pressure (measurement) value is used which was also determined when evaluating the pressure prevailing in the arterial and in the venous blood line, in particular subsequent to a statistical evaluation, by forming the sum and/or the average value.

In some embodiments, the determined reference pressure measurement values are compared with at least one data set from at least one previous treatment session from the same patient and/or reference pressure (measurement) values recorded from previous treatment sessions of other patients.

In some embodiments, the determined reference pressure measurement values are used as reference pressure measurement values for treatment, preferably if and only if the comparison with data sets of or from past treatment sessions satisfies predetermined criteria, in particular expected values or expected value ranges obtained from the data sets.

Several or all of the embodiments according to the present disclosure may have one, more, or all of the advantages listed above and/or in the following.

An advantage of the present systems, methods, and devices may be that intratherapeutically occurring pressure measurement values, which would conventionally be sufficient to trigger a pressure alarm, are first subject to an assessment as described herein, which is why objectively uncritical pressure measurement values do not already lead to an alarm, which requires attention, time and effort from medical personnel. According to the present disclosure, it may thus be possible to automatically recognize one or the other supposed alarm event as such, which, on closer inspection, does not denote a condition that would require an intervention. Since it can be recognized automatically, personnel costs can be reduced, material resources can be saved (changing gloves while treating a first patient and eliminating a—supposed—alarm condition with a second patient), and hygienic risks can be minimized, as explained below.

Furthermore, the alarm range or the alarm criteria can be set comparatively more narrowly and/or patient-specifically by the individual assessment of pressure measurement values that are inherently suspicious of alarm and/or due to the evaluation of such pressure measurement values supplemented according to the present disclosure. This setting is possible because reference pressure (measurement) values, or reference characteristic lines, are recorded at the beginning of the treatment. By this targeted recording of the current reference pressure (measurement) values or reference characteristic lines, thus, patient-specific conditions and those dependent on the patient's condition are recorded and taken into account. These can lead to individually adapted alarm criteria, which is also encompassed by the present disclosure. Possible general conditions that lead to different reference pressure (measurement) values, or reference characteristic lines, include, among others, the size of the needle used, the type of fistula and, in particular, the blood viscosity of the patient, especially at the beginning of the blood treatment session.

Advantageously, the system's assessment of the alarm based on combinatorial methods of sensor analysis increases patient safety by reducing the risk of misinterpretation of alarms.

Another further advantage of the present disclosure may be that by avoiding unnecessary alarms on the blood treatment apparatus, the ease of use of the same is increased. Ease of use increases when false alarms can be suppressed.

As the condition of a patient can advantageously be checked in a targeted manner using the present systems, methods, and devices, the patient's safety can be increased.

Another advantage can be that by avoiding frequent and/or unnecessary alarms, thereby frequent and/or unnecessary contact with the blood treatment apparatus by the treating personnel can also be avoided. A reduction in human-machine contacts advantageously leads to better hygiene and the avoidance of contamination among the participants in the clinical routine, which indirectly also increases patient safety. In this context, the use of disposable gloves, in particular for acknowledging alarms, can advantageously be reduced and thus further costs can be saved.

The cases managed using the present systems, methods, and devices, in which supposed alarm conditions are recognized as such and are not brought to the attention of medical personnel or not without comment, advantageously significantly reduce the interaction of medical personnel in the event of a non-critical pressure pattern. It is estimated that self-analysis of pressure alarms reduces the noticeable interruption of treatment by about 70%, and treatment advantageously appears calmer, especially for the patient. When the 'noticeable' alarm frequency is reduced, the actual relevance of the now remaining visible alarms becomes much higher. The user can read a message text and react adequately to it.

A further advantage of the present systems, methods, and devices may be the safe clarification of abnormal irregularities, preferably avoiding any audio-visual alarm output where this is not required, helps to counteract so-called 'alarm fatigue'. 'Alarm fatigue' is the lack of attention to alarms due to the frequency of their occurrence. The hazard risk associated with 'alarm fatigue' was listed by the Emergency Care Research Institute (ECRI) in 2008 as one of the top ten hazards associated with technology in ICUs (https://auriga.com/blog/2020/alarm-fatigue/).

The present systems, methods, and devices are easy to implement in existing systems because, according to the present disclosure, regular devices already present on conventional blood treatment apparatuses, such as blood pump, dialysate pump, pressure meters or sensors, tubing clamps, etc., can be used or the present systems, methods, and devices can be implemented using them. Retrofitting of existing blood treatment apparatuses is also possible in a simple manner via software updates.

BRIEF DESCRIPTION OF THE DRAWINGS

The present disclosure is exemplarily explained with regard to the accompanying drawing, in which identical reference numerals refer to the same or similar components. In the figures.

Figure 3A:
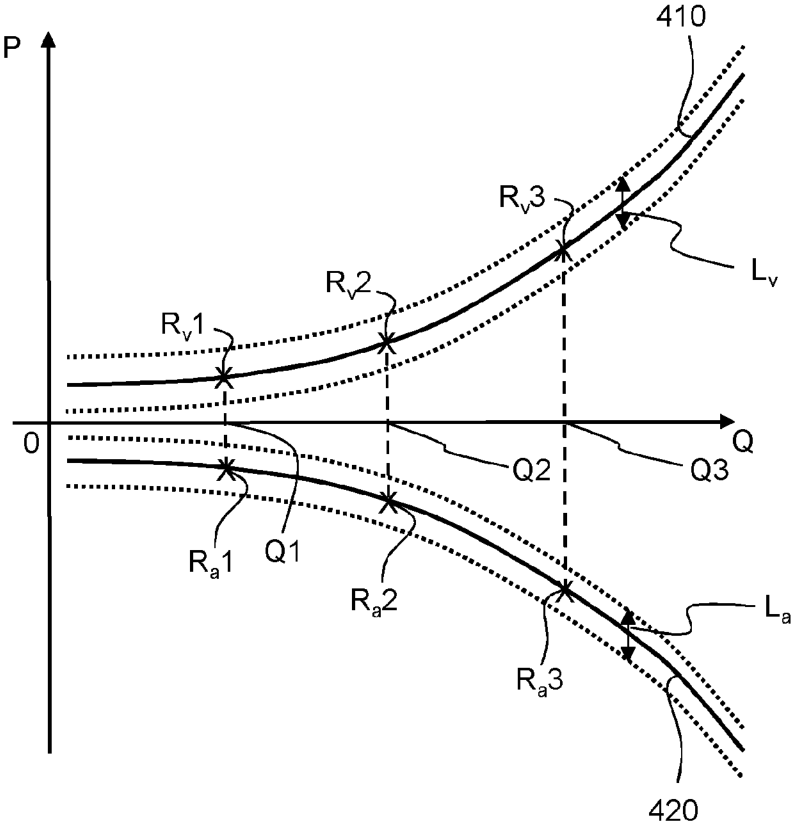
Figure 4:
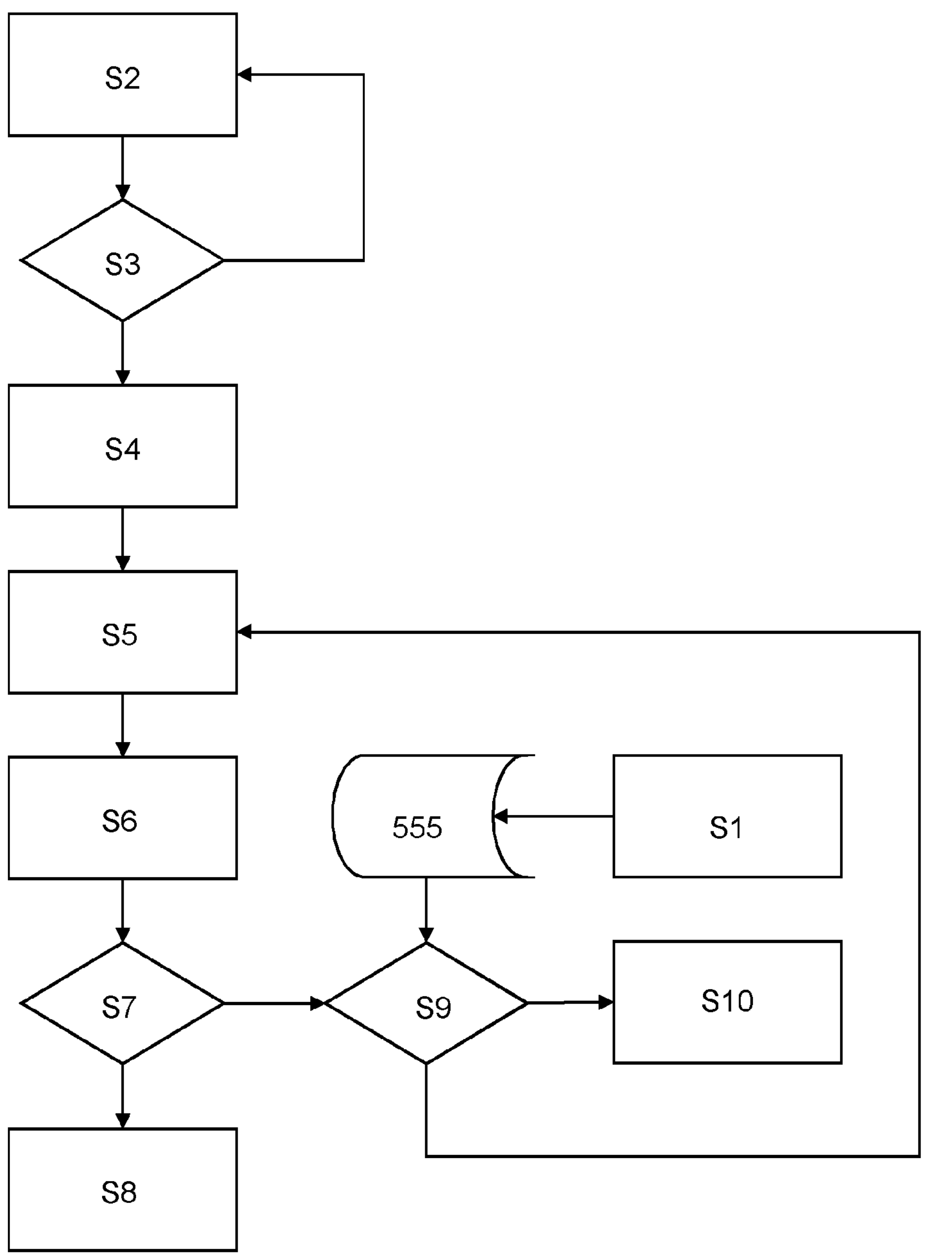

FIG. **3*a*** shows schematically simplified typical reference pressure profiles as they could be or were recorded at the beginning of the method described herein;

FIG. **3*b* shows in the representation of the reference pressure profiles from FIG. 3*a* additional assessment pressure measurement values Bax, Bvx for assessing an alarm event; and FIG. 4** shows, in a highly simplified representation, a flow diagram of a medical method in a first embodiment.

DETAILED DESCRIPTION

Figure 1:
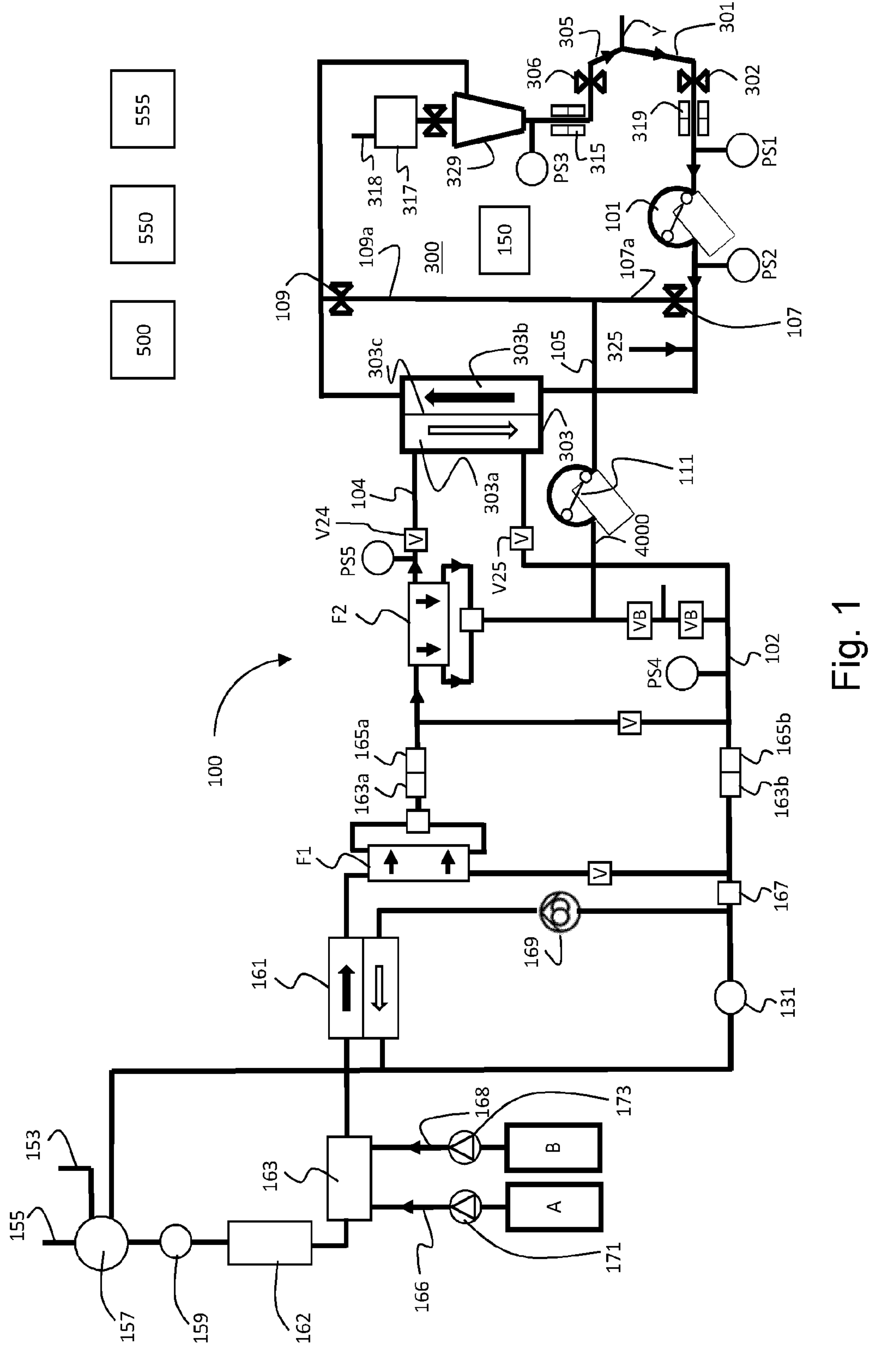
FIG. 1 shows schematically simplified a fluid line structure of a blood treatment apparatus in a first embodiment.

FIG. 1 shows schematically simplified fluid line structure of a blood treatment apparatus 100 in a first, purely exemplary embodiment. Other embodiments of the blood treatment apparatus 100 than those shown herein are also encompassed by the present disclosure.

The blood treatment apparatus 100 is connected to an extracorporeal blood circuit 300, which can be connected to the vascular system of the patient, not shown, for a treatment using double-needle access, or via single-needle access using, for example, an additional Y-connector (reference numeral Y) as shown in FIG. 1. The blood circuit 300 may be present, optionally in sections, in or on a blood cassette.

Pumps, actuators and/or valves, for example, in the area of the blood circuit 300 are connected in signal communication or signal connection, or prepared therefor, with the blood treatment apparatus 100 or to a control device 150 (which optionally may be a closed-loop control device) optionally encompassed by it.

The blood circuit 300 includes or is connected to an arterial patient tubing clamp 302 on an arterial section or an arterial patient line, blood withdrawal line or arterial blood line 301, here connected to an arterial connection needle. The blood circuit 300 further includes or is connected to a venous patient tubing clamp 306 on a venous section or a venous patient line, blood return line or venous line 305, here connected to a venous connection needle.

A blood pump 101 is provided in or at the arterial blood line 301, a substitute fluid pump 111 is connected to a dialysis liquid inlet line 104 for conveying fresh dialysis liquid, which is filtered in a further filter stage (F2) (substitute fluid). A substitute fluid line 105 may be fluidically connected to the inlet line 104. Using the substitute fluid pump 111, substitute fluid may be introduced by pre-dilution, via a pre-dilution valve 107, or by post-dilution, via a post-dilution valve 109, via associated lines 107*a* or 109*a* into line sections, for example into the arterial blood line 301 or into the venous blood line 305 (here between a blood chamber 303*b* of a blood filter 303 and a venous air separation chamber or venous blood chamber 329) of the blood circuit 300.

The blood filter 303 includes the blood chamber 303*b* connected to the arterial blood line 301 and to the venous blood line 305. A dialysis liquid chamber 303*a* of the blood filter 303 is connected to the dialysis liquid inlet line 104 which leads to the dialysis liquid chamber 303*a* and to a dialysate outlet line 102 which leads away from the dialysis liquid chamber 303*a*, which conveys dialysate, i.e., used dialysis liquid. For this purpose, suitable connectors are used on the dialysis liquid inlet line 104 or on the dialysate outlet line 102 on the one hand and on the dialysate ports on the other hand, which can be connected to one another, in particular in a detachable manner.

Dialysis liquid chamber 303*a* and blood chamber 303*b* are separated from each other by a mostly semi-permeable membrane 303*c*. It represents the partition between the blood side with the extracorporeal blood circuit 300 and the machine side with the dialysis liquid or dialysate circuit, which is shown in FIG. 1 to the left of the membrane 303*c*.

The arrangement in FIG. 1 optionally further includes a valve V24, which is arranged in the dialysis liquid inlet line 104 upstream of the blood filter 303 but downstream of a pressure sensor PS5. It optionally further includes a valve V25, which is arranged in the dialysate outlet line 102, downstream of the blood filter 303, but upstream of a further pressure sensor FIG. PS4.

The arrangement in FIG. 1 includes an optional detector 315 for detecting air and/or blood. The arrangement in FIG. 1 further encompasses at least one or more pressure sensors, here the pressure meter or pressure sensor PS1 (here exemplarily, upstream of the blood pump 101) and PS2 (here exemplarily, downstream of the blood pump 101, it measures the pressure upstream of the blood filter 303 ("prehemofilter")) at the points shown in FIG. 1. Similarly, a further venous pressure meter PS3 is also provided, for example downstream of the venous blood chamber 329. Further pressure sensors can be provided. Of the aforementioned pressure meters PS1 and PS3, only one is mandatory, the remaining others can each be provided optionally.

An optional single-needle chamber 317 is used in FIG. 1 as a buffer and/or compensating reservoir in a single-needle procedure in which the patient is connected to the extracorporeal blood circuit 300 using only one of the two blood lines 301, 305.

The arrangement of FIG. 1 also includes an optional detector 319 for detecting air bubbles and/or blood.

An optional addition site 325 for Heparin or for other anticoagulants may be provided.

On the left in FIG. 1, is shown an optional mixing device 163, which provides a predetermined mixture for the respective solution from the containers A (for A-concentrate via concentrate supply 166) and B (for B-concentrate via concentrate supply 168) for use by the blood treatment apparatus 100. The solution contains water from a water source 155 (on-line, e.g., as reverse osmosis water or from bags) which is heated, for example, in an optional heating device 162.

An optional pump 171, which can be referred to as a concentrate pump or a sodium pump, is fluidically connected to the mixing device 163 and a source of sodium, for example the container A, and/or conveys out of it. An optional pump 173, associated with container B, e.g., for bicarbonate, can also be seen.

Furthermore, FIG. 1 shows a waste outlet 153 for the effluent. An optional heat exchanger 157 and a first flow pump 159, which is suitable for de-gassing, complete the arrangement shown.

The pressure sensor PS4 downstream of the blood filter 303 on the water side, but preferably upstream the ultrafiltration pump 131 in the dialysate outlet line 102 may be provided for measuring the filtrate pressure or membrane pressure of the blood filter 303.

Blood that leaves the blood filter 303 flows through an optional venous blood chamber 329, which may include a de-aeration device 318 and may be in fluid communication with the pressure sensor PS3.

The exemplary arrangement shown in FIG. 1 includes the control device 150 which may be a closed-loop control device. It may be in a wired or wireless signal connection with any of the components mentioned herein—especially or in particular with the blood pump 101—to control or regulate the blood treatment apparatus 100

By using the device for on-line mixing of the dialysis liquid, a variation of its sodium content, controlled by the control device 150, is possible within certain limits. For this purpose, in particular the measurement values determined by the conductivity sensors 163*a*, 163*b* may be taken into account. Should an adjustment of the sodium content of the dialysis liquid (sodium concentration) or of the substitute fluid turn out to be necessary or desired, this can be done by adjusting the conveying rate of the sodium pump 171.

In addition, the blood treatment apparatus 100 includes devices for conveying fresh dialysis liquid and dialysate. So for example, valve V24 may be provided between the first flow pump 159 and the blood filter 303, which opens or closes the inlet to the blood filter 303 on the inlet side. A second, optional flow pump 169 is provided, for example, downstream of the blood filter 303, which conveys dialysate to the waste outlet 153. The valve V25 can be provided between the blood filter 303 and the second flow pump 169, which opens or closes the drain on the outlet side.

Furthermore, the blood treatment apparatus 100 optionally includes a device 161 for balancing the flow flowing into and out of the dialyzer 303 on the machine side. The device 161 for balancing is preferably arranged in a line section between the first flow pump 159 and the second flow pump 169.

The blood treatment apparatus 100 further includes devices, such as the ultrafiltration pump 131, for the precise removal of a volume of liquid from the balanced circuit, as predetermined by the user and/or by the control device 150.

Sensors such as the optional conductivity sensors 163*a*, 163*b* serve to determine the conductivity, which in some embodiments is temperature-compensated, as well as the liquid flow upstream and downstream of the dialyzer 303.

Temperature sensors 165*a*, 165*b* may be provided as one or a plurality thereof. Temperature values supplied by them may be used to determine a temperature-compensated conductivity.

A leakage sensor 167 is optionally provided. Alternatively, it may also be provided at a different location.

Further flow pumps in addition to or alternatively to, e.g., the one with the reference numeral 169 may also be provided.

A number of optional valves are each denoted with V in FIG. 1; by-pass valves with VB.

Based on the measurement values of the above-mentioned, optional sensors, the control device 150 determines in some embodiments the electrolyte and/or fluid balance.

Filters F1 and F2 can be provided connected in series.

Even when using non-pure water, the filter F1 exemplarily serves herein to generate sufficiently pure dialysis liquid by the mixing device 163, which then flows through the blood filter 303, e.g., using the countercurrent principle.

The filter F2 exemplarily serves herein to generate sterile or sufficiently filtered substitute fluid from the sufficiently pure dialysis liquid leaving the first filter F1, by filtering, e.g., pyrogenic substances. This substitute fluid may then be safely added to the extracorporeally flowing blood of the patient and thus ultimately to the patient's body.

An alarm output device 500, an alarm criterion memory 550, and a reference data memory 555 are indicated in the upper right corner of FIG. 1. These devices may be in signal communication or signal connection with each other and/or with components of the blood treatment apparatus 100, in particular its control device 150, or may be prepared for this purpose.

Figure 2:
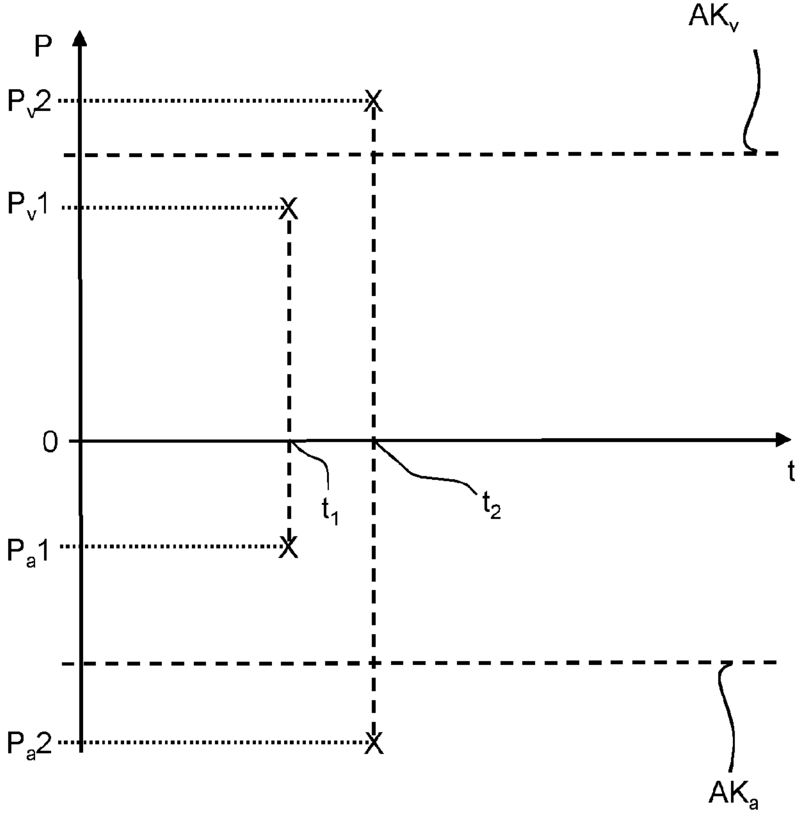
FIG. 2 shows schematically simplified an assessment of whether a determined pressure measurement value satisfies an alarm criterion, in an exemplary embodiment.

The alarm output device 500 is used to output an alarm or pressure alarm, particularly to medical personnel, based on the pressure measurement value Pvx, Pax currently detected in the arterial blood line 301 and/or the venous blood line 305 (see FIG. 2).

The alarm criterion memory 550 is used to store at least one predetermined alarm criterion AKa, AKv (see FIG. 2), which defines an alarm event.

The reference data memory 555 includes at least one data set that in turn contains or includes one or more reference pressure profiles 410, 420 or reference pressure (measurement) values $R_v x$, $R_a x$ (see FIG. 3).

The blood treatment apparatus 100 is optionally shown in FIG. 1 as a device for hemo(dia)filtration. However, hemodialysis devices, as well as blood treatment apparatuses which function differently, are also covered by the present disclosure, although not specifically represented in a figure.

The present disclosure is not limited to the embodiment described above, which is for illustrative purposes only.

The arrows shown in FIG. 1 generally indicate the direction of flow in each case.

FIG. 2 shows schematically simplified an assessment of whether a measured pressure value Pv1, Pv2, Pa1, Pa2 measured during a blood treatment session, during which the blood pump 101 conveys at an initial conveying rate or is set to do so, satisfies an alarm criterion AKv, AKa, i.e., whether the latter is fulfilled, in an exemplary embodiment.

In the diagram of FIG. 2, the pressure P is shown over the time t. The alarm criteria AKv, AKa have been defined here in exemplary embodiment as reaching, exceeding or falling below certain pressure measurement values for the pressure in the arterial blood line 301 or in the venous blood line 305 of the extracorporeal blood tubing set 300 of the blood treatment apparatus 100. They are stored in the alarm criteria memory 550 (see FIG. 1).

In the example of FIG. 2, the prevailing pressure in the arterial blood line 301 and in the venous blood line 305 are measured at two different times t1, t2, respectively.

For time t1, there is a pressure measurement value Pa1 in the arterial blood line 301 and a pressure measurement value Pv1 in the venous blood line 305 of the blood tubing set 300. As can be seen from FIG. 2, the pressure measurement value Pa1 in the arterial blood line 301 is above the alarm criterion AKa, and the pressure measurement value Pv1 in the venous blood line 305 is below the alarm criterion AKv. Accordingly, in this example, no alarm criterion AKv, AKa is fulfilled. Thus, there is no alarm event, no alarm would be issued. Above all, the blood pump 101 (not shown here, see FIG. 1) would not be stopped or its conveying rate would not be lowered in accordance with the present disclosure, as is the case for subsequent pressure measurement values other than Pa1, Pv1.

For the time point t2, a pressure measurement value Pa2 in the arterial blood line 301 or a pressure measurement value Pv2 in the venous blood line 305 of the blood tubing set 300 was measured, respectively. As can be seen from the diagram in FIG. 2, the pressure measurement value Pa2 in the arterial blood line 301 is below the alarm criterion AK a and the pressure measurement value Pv2 in the venous blood line 305 is above the alarm criterion $AK_v$. In this example, two alarm criteria $AK_v$, $AK_a$ would be met—independently of one another. In this case, the blood pump 101 would be stopped or its conveying rate would be reduced in order to carry out an assessment of the relevance of the measured pressure measurement values Pa2 and Pv2. This is described in more detail for FIGS. 3 and 4.

Alternatively or additionally, an evaluation, in particular an averaging or the sum of arterial pressure measurement value and venous pressure measurement value can be compared with an alarm criterion (not shown here).

In particular, a deviation of the sum of arterial pressure measurement value and venous pressure measurement value from reference pressure (measurement) values or ranges can indicate the condition as well as the development of the condition of the fistula, in particular the presence or the risk of a stenosis. For example, if the sum of the arterial and venous pressure measurement values is, for example, greater than the reference pressure (measurement) value or is outside the reference pressure range, this may be an indication of a venous stenosis.

An arterial stenosis could be indicated by a low or comparatively low sum of arterial and venous pressure measurement values.

A combination of assessments or checks is also possible, so that the sum of the two aforementioned pressure measurement values and one or both individual pressure measurement values are compared with alarm criteria. The alarm criteria can differ depending on the type of measured pressure measurement value. The alarm criteria can also be formed from a pressure measurement value range with upper and lower threshold values.

As in the example in FIG. 2, the definition of the alarm criteria AKv, AKa can encompass exceeding or falling below threshold values. Alternatively or additionally, threshold ranges can also be defined, in the present example the area between AKv and Aka for example, which may not be exceeded.

In certain embodiments, threshold ranges can be defined into which measured pressure measurement values may not fall. In the present example, these would be the ranges above AKv and below AKa. The alarm criteria can be adjusted during treatment.

FIG. 3*a* shows schematically simplified typical reference pressure profiles 410, 420 (e.g. in [mbar] or [hPa] over the conveying rate Q (e.g. in [ml/min])) of the blood pump 101, here in the form of pressure-flow characteristic lines, as they are recorded at the beginning of the method described herein and could be available as a reference during the treatment session.

To create the two reference pressure profiles 410, 420, reference pressure measurement values $R_v x$, $R_a x$, (x=1, x=2, x=3, x=4) (here: pressure-flow pairs) are initially determined at the beginning of the treatment by determining several times the pressure in the blood tubing set 300 of the blood treatment apparatus 100—here exemplarily both in the arterial blood line 301 and in the venous blood line 305 of the blood tubing set 300—while the blood pump 101 (see FIG. 1) conveys at one (here: three) different reference conveying rates Q1, Q2, Q3, respectively. The reference pressure measurement values $R_v x$, $R_a x$ determined in each case for the different reference conveying rates Q1, Q2, Q3 are stored in a suitable reference data memory 555 provided for this purpose. The reference pressure profiles 410, 420 to be created can thus already be available at this point, i.e., after two, three (as in the example in FIG. 3*a*) or more reference pressure measurement values $R_v x$, $R_a x$ have been determined.

Alternatively or additionally, continuous or solid curves or characteristic lines can be calculated or recorded from the different reference conveying rates Q1, Q2, Q3 accessed via the blood pump 101 and the reference pressure measurement values $R_v x$, $R_a x$ determined for each of these. Those are shown in FIG. 3*a* purely optionally and can serve as reference pressure profiles.

In certain embodiments, the historical data of the patient to be treated and/or data of a patient collective is additionally or alternatively used for creating references.

Alternatively or additionally, further processing of the determined reference pressure measurement values $R_v x$, $R_a x$ can yield reference intervals $L_a$, $L_v$. These intervals can play a role in the subsequent evaluation of assessment pressure measurement values and in the determination of evaluation results.

For example, the reference pressure measurement values $R_v x$, $R_a x$ are determined at the beginning of the blood treatment session by increasing the conveying rate of the blood pump 101 and repeatedly measuring the pressures prevailing at the individual conveying rates or by decreasing the conveying rate of the blood pump 101 and repeatedly measuring the pressures prevailing at the individual conveying rates, in each case as reference pressure measurement values $R_v x$, $R_a x$.

The hysteresis that occurs can itself serve as a reference interval for comparing the assessment measurement values recorded later in the treatment.

In this the hysteresis profiles themselves can serve as a reference interval, for example, by optionally multiplying the profiles by a factor. This factor can basically assume different values for upper or lower deviations. Alternatively or additionally, the reference pressure measurement values can be used after equilibrating the pressures at certain blood flow rates. The confidence interval can be formed around these reference pressure measurement values, or characteristic lines. The interval can be formed proportional to the pressure value or as an absolute distance from the reference pressure measurement value. The breadth of a reference interval can be selected to be constant or variable (depending on the flow rate).

The gathering of the reference pressure measurement values $R_v x$, $R_a x$ at the beginning of the treatment has the advantage that, in comparison with, for example, manufacturer-set threshold values, the patient-specific conditions of the current treatment, for example the size of the needle used, the special features of the fistula and, in particular, the patient's blood viscosity, can be taken into account. As a result, more accurate reference pressure measurement values $R_v x$, $R_a x$ can be obtained for the reference pressure profile 410, 420. The reference pressure profile 410, 420 can be recorded separately for both the arterial blood line 301 and the venous blood line 305 of the blood tubing set and stored in the reference data memory 555 Processing of the reference pressure measurement values $R_v x$, $R_a x$, for example by determining and storing a reference pressure profile from the sum of the respective associated reference pressure measurement values $R_v x$, $R_a x$, is also encompassed by the present disclosure. In such embodiments, a total of three or more different reference pressure profiles/characteristic lines may be available individually or in any combination for the purpose of assessment of assessment pressure measurement values $B_v x$, $B_a x$ or their sums. In particular, the determined pressure-flow pairs (also: pressure-flow value pairs) or a characteristic line created from them can be stored. Alternatively or additionally, the parameters of a characteristic line approximation can be stored. This and other approximations, as mentioned herein, can be achieved by splinefit, interpolation or polynomial approximation.

In certain embodiments, historical data of the patient to be treated and/or data of a patient collective are additionally or alternatively used for the plausibility check. For this purpose, for example, the reference pressure measurement values or reference pressure profiles recorded at the beginning of a treatment session are compared with stored reference pressure (measurement) values or reference pressure (measurement) profiles of previous treatment sessions of the same patient. If there is a large deviation—e.g., measured against predetermined criteria—or a deviation that satisfies the predetermined criteria, i.e., a deviation that, for example, exceeds a predetermined threshold value, an alarm can already be issued at this point. For example, this comparison or check of the reference pressure (measurement) values or reference pressure profiles can be used to identify an incorrectly positioned needle.

In the example of FIG. 3*a*, the reference pressure profiles 410, 420 are shown as solid (characteristic) lines. The reference pressure profiles 410, 420 were determined, as explained herein, based on reference pressure measurement values $R_vx$, $R_ax$ (x=1, x=2, x=3) collected at the beginning of the treatment. The limits of the optional reference intervals $L_v$, $L_a$, also determined based on these values, are represented by dotted lines.

Figure 3B:
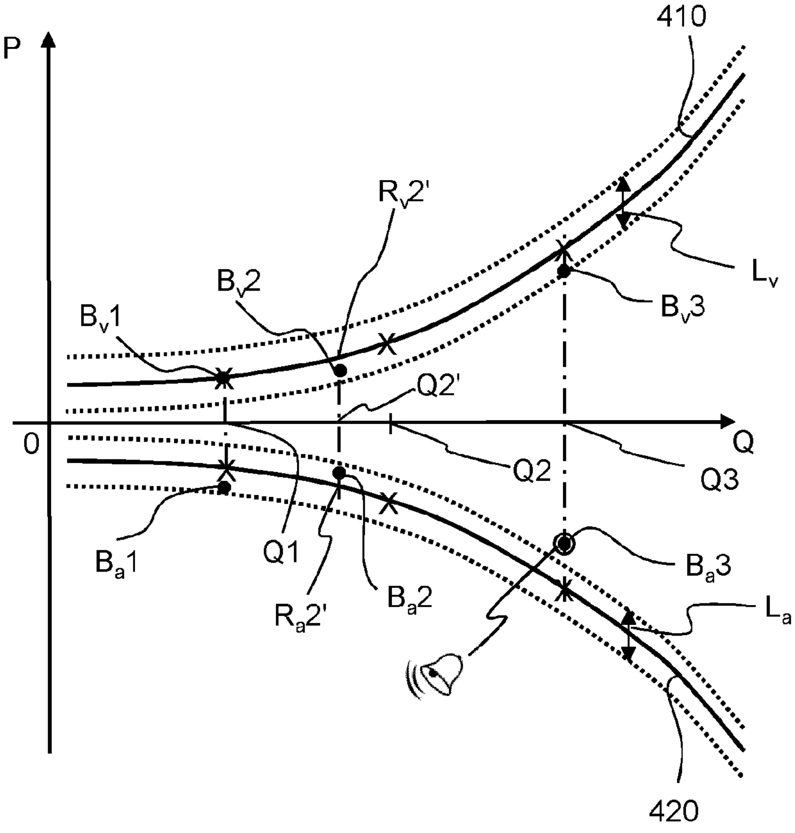

FIG. 3*b* shows the reference pressure profiles 410, 420 from FIG. 3*a*. In FIG. 3*b*, additionally, assessment pressure measurement values $B_vx$, $B_ax$ for assessing an alarm event are shown.

If a pressure measurement value $P_vx$, $P_ax$ measured during the treatment has met at least one alarm criterion, as shown in FIG. 2 for the pressure measurement values $P_v$2 $P_a$2 for example, then according to the present disclosure the current blood treatment regime is deviated from by stopping or at least slowing down the blood pump 101. While the conveying rate of the blood pump 101 is subsequently gradually increased again, the pressure currently prevailing in the arterial blood line 301 and/or the venous blood line 305 of the blood tubing set 300 is measured at different reference conveying rates Qx, respectively, analogously to determining the reference pressure measurement values $R_vx$, $R_ax$ as carried out at the beginning of the treatment and discussed with reference to FIG. 3*a*, which is referred to herein as the assessment pressure measurement value $B_vx$ or $B_ax$, respectively. FIG. 3*b* shows, by way of example only, six such assessment pressure measurement values $B_v$1, $B_v$2, $B_v$3 as well as $B_a$1, $B_a$2 and $B_a$3, measured at three different reference conveying rates Q1, Q2', and Q3.

Each of the measured assessment pressure measurement values $B_vx$ or $B_ax$, each of which can be assigned to a particular reference conveying rate Qx of the blood pump 101 readable from FIG. 3*a* or FIG. 3*b*, can be used for assessment, in particular in which it is compared to or otherwise correlated/linked to the reference pressure (measurement) value $R_vx$, $R_ax$, associated with the same reference conveying rate Qx, readable from the reference pressure profiles 410, 420.

This correlation can in particular encompass forming a difference between the assessment pressure (measurement) value $B_vx$, $B_ax$, and the one or more reference pressure (measurement) values $R_vx$, $R_ax$ in the data set of the reference data memory 555, or with the reference pressure profile(s) 410, 420 created therefrom.

It can be seen from the example in FIG. 3*b* that the venous assessment pressure (measurement) value $B_v$1 determined under the first reference conveying rate Q1 corresponds exactly to the reference pressure (measurement) value $R_v$1. The arterial assessment pressure (measurement) value $B_v$1 determined for the same reference conveying rate Q1 is still within the reference pressure interval $L_a$. Up to this point in time of the ongoing assessment process, no alarm event would be confirmed or no alarm would be triggered.

FIG. 3*b* makes it clear that assessment pressure measurement values $B_vx$ or $B_ax$ cannot only be collected for reference conveying rates Qx of the blood pump 101, for which reference pressure (measurement) values $R_vx$ or $R_ax$ were already measured beforehand. Rather, assessment pressure measurement values $B_vx$ or $B_ax$ can also be collected for reference conveying rates Qx, which lie between reference conveying rates Qx, for which specifically no reference pressure (measurement) values $R_vx$ or $R_ax$ were measured, but whose reference pressure values were determined based on the reference pressure (measurement) value $R_vx$ or $R_ax$, for example by interpolation.

The latter assessment pressure measurement values include the assessment pressure measurement values $B_v$2 and $B_a$2. The reference conveying rate Q2' at which they are measured lies between Q1 and Q2. The reference pressure values Rv2' and Ra2' required for their assessment can be read from the reference pressure profiles 410, 420, which have been completed to form characteristic lines.

The assessment pressure (measurement) values $B_a$2, $B_v$2 determined for the reference conveying rate Q2', which lies between the reference conveying rate Q1 and the reference conveying rate Q2, also lie in the respective reference pressure interval $L_a$, $L_v$. They would also not represent a confirmation of an alarm event, i.e., would not trigger an alarm.

Of the assessment pressure measurement values $B_a$3, $B_v$3, determined in FIG. 3*b* at the third reference conveying rate Q3, only the venous assessment pressure measurement value $B_v$3 still lies in the reference pressure interval $L_v$, while the arterial assessment pressure measurement value $B_a$3 lies above or outside the reference pressure interval $L_a$.

The evaluation of the assessment pressure measurement value $B_a$3 with regard to the reference pressure interval L a shows that the predetermined requirements for the output of an alarm are satisfied. As shown in FIG. 3*b* for the assessment pressure measurement value $B_a$3 via the alarm icon, a pressure alarm can now be output. The trigger for this was therefore not one of the pressure values measured during the treatment, as shown in FIG. 2, but only the assessment pressure measurement value $B_a$3 from the subsequent assessment method described herein.

In such a case, the alarm event is therefore confirmed and an alarm to the medical personnel would be initiated. The medical personnel can, in such a case then proceed with the usual procedures for handling or eliminating an alarm.

If all assessment pressure measurement values $B_vx$, $B_ax$ are within the reference pressure intervals $L_v$, $L_a$ the treatment would continue without confirming the alarm event or without (further) causing an alarm.

In this case, no alarm can be issued and the medical staff cannot be informed at least audibly, visually and/or in other ways that may be perceived as distracting, that pressure measurement values have in the meantime satisfied the alarm criterion, e.g., they have exceeded or fallen below threshold values (see FIG. 2). Alternatively, the medical staff can be informed that pressure measurement values have meanwhile met the alarm criterion (see FIG. 2). Such an indication can be a message that the result of the method described herein has not confirmed the alarm event. It can be designed in such a way that—unlike actual alarms—it does not require human intervention such as confirmation, termination or handling of the alarm (e.g., by definition, e.g., as specified in the manual).

FIG. 4 shows in a highly simplified representation a flow diagram of the method described herein in a first embodiment.

The method shown is optionally preceded by the features of providing a blood treatment apparatus 100, an alarm criteria memory 550 and a reference data memory 555, in particular as set forth with respect to FIG. 1. In the following, reference is made to the reference signs in the previous figures.

The feature S1 represents determining reference pressure (measurement) values $R_v x$, $R_a x$ (pressure-flow pairs) at the beginning of the treatment in the arterial blood line 301 and/or the venous blood line 305, in particular as set forth herein in connection with predetermined flow rates of the blood pump 101. It further encompasses storing these reference pressure (measurement) values $R_v x$, $R_a x$, directly or further processed, for example as reference data profiles 410, 420 or reference intervals $L_a$, $L_v$, as data sets in a reference data memory 555 provided and suitable for this purpose. In certain embodiments, historical data of the patient to be treated and/or data of a patient collective are additionally used for reference formation.

The monitoring of the blood treatment is represented by the following features, wherein during feature S2, in particular at regular intervals, the prevailing pressures in the arterial blood line 301 and/or in the venous blood line 305 are determined as pressure measurement values $P_v x$, $P_a x$ by the pressure meters PS1 and PS3 provided there.

In feature S3, the question is clarified as to whether the determined pressure measurement values $P_v x$, $P_a x$ meet predetermined alarm criteria $AK_a$, $AK_v$, which are stored in the alarm criterion memory 550 and define an alarm event.

If the pressure measurement values $P_v x$, $P_a x$ do not meet any alarm criteria $AK_a$, $AK_v$ (no event), the treatment is continued and the process returns to feature S2.

If the pressure measurement values $P_v x$, $P_a x$ meet an alarm criterion $AK_a$ and/or $AK_v$ (yes event), the blood pump 101 is stopped in feature S4 or, alternatively, its conveying rate is slowed down so that it is below a predetermined initial conveying rate. In this case, no alarm can be issued and the medical staff cannot be alerted, at least audibly, visually and/or in other ways that may be perceived as distracting, that pressure measurement values had in the meantime satisfied the alarm criterion.

Feature S5 represents increasing a reference conveying rate of the blood pump 101, in particular analogously to the reference conveying rates when determining the reference pressure (measurement) values $R_v x$, $R_a x$ before the start of the treatment.

In feature S6, at the reference conveying rate of the blood pump 101, the respective prevailing pressure is measured in the arterial blood line 301 and/or in the venous blood line 305 using the corresponding pressure meters PS1, PS3, and thus assessment pressure measurement values $B_v x$, $B_a x$ are determined.

As long as a critical pressure or the maximum conveying rate of the blood pump 101 has not yet been reached (check in feature S7), in feature S9, the determined assessment pressure measurement values $B_v x$, $B_a x$ are compared with the reference pressure profiles 410, 420, with the reference pressure (measurement) values $R_v x$, $R_a x$ or the reference intervals $L_a$, $L_v$ from the reference data memory 555 and the question is clarified as to whether the assessment pressure measurement values $B_v x$, $B_a x$, remain within the reference intervals $L_a$, $L_v$.

If the assessment pressure measurement values $B_v x$, $B_a x$ are within the reference intervals $L_a$, $L_v$, the system returns to feature S5 and the conveying rate of the blood pump is further increased in accordance with the method described herein.

If the assessment pressure measurement values $B_v x$, $B_a x$ are outside the reference intervals $L_a$, $L_v$, an audible, visual or haptic alarm, particularly a nurse request, particularly for a person being treated, is initiated in feature S10.

If the check in feature S7 shows that a critical pressure or the maximum conveying rate of the blood pump 101 has been reached and that all assessment pressure measurement values $B_v x$, $B_a x$ are within the reference pressure intervals $L_a$, $L_v$, the treatment is continued (feature S10).

In this case, no alarm can be issued and the medical staff cannot be informed, at least audibly, visually and/or in any other way that may be perceived as distracting, that pressure measurement values have in the meantime satisfied the alarm criterion, e.g., because they have in the meantime exceeded or fallen below a threshold value (see. FIG. 2).

Alternatively, the medical staff can be informed that pressure measurement values have in the meantime satisfied the alarm criterion. Such an indication can be a message that the result of the method described herein has not confirmed the alarm event. It can be designed in such a way that it does not require any human action.

LIST OF REFERENCE NUMERALS

100 blood treatment apparatus
101 blood pump
102 dialysate outlet line
104 dialysis liquid inlet line
105 substitute fluid line
107 pre-dilution valve
107*a* line leading or belonging to the pre-dilution valve
109 post-dilution valve
109*a* line leading to or belonging to the post-dilution valve
111 substitute fluid pump
131 ultrafiltration pump
150 control device
153 waste outlet
155 water source
157 heat exchanger
159 first flow pump
161 balancing device
162 heating device
163 mixing device
163*a* conductivity sensor
163*b* conductivity sensor
165*a* temperature sensor
165*b* temperature sensor
166 concentrate supply
167 leakage sensor
168 concentrate supply
169 second flow pump
171 pump; sodium pump
173 pump; bicarbonate pump
300 extracorporeal blood circuit
301 arterial blood line
302 (first) tubing clamp
303 blood filter or dialyzer
303*a* dialysis liquid chamber
303*b* blood chamber
303*c* semi-permeable membrane
305 venous blood line
306 (second) tubing clamp
315 detector
317 single-needle chamber
318 de-aeration device
319 detector
325 addition site for Heparin, anticoagulant
329 venous blood chamber (optional)
410 reference pressure profile in the venous line
420 reference pressure profile in the arterial line
500 alarm output device
550 alarm criterion memory 555 reference data memory
F1 filter
F2 filter
A container for A-concentrate; sodium
B container for B-concenrate; bicarbonate
$AK_a$, $AK_v$ alarm criterion
$L_a$, $L_v$ reference interval
P pressure measurement sites
PS1 arterial pressure meter (optional)
PS2 arterial pressure sensor (optional)
PS3 pressure meter (optional)
PS4 second pressure sensor for measuring the filtrate pressure (optional)
PS5 pressure sensor for measuring the pressure in the dialysis liquid inlet line
$B_a x$ assessment pressure measurement value from the measurement in the arterial blood line
$B_v x$ assessment pressure measurement value from the measurement in the venous blood line
$P_a x$ pressure measurement value when measuring in the arterial blood line
$P_v x$ pressure measurement value when measuring in the venous blood line
Q1 to Q3 reference conveying rates
Q2' reference conveying rate
$R_a x$ reference pressure (measurement) value for the measurement in the arterial line
$R_v x$ reference pressure (measurement) value for the measurement in the venous line
$R_a 2'$ reference pressure (measurement) value for the measurement in the arterial line
$R_v 2'$ reference pressure value for the measurement in the arterial line
S1 to S10 method features
V valves
V24 valve
V25 valve
VB bypass valve
Y Y-connector

The invention claimed is:

1. A method for assessing a measured pressure value, the method comprising:

providing a blood treatment apparatus, connectable to a blood tubing set comprising an arterial blood line and a venous blood line, the blood treatment apparatus comprising:

a blood pump for conveying blood extracorporeally along the arterial blood line, an arterial pressure meter for measuring an arterial pressure in the arterial blood line and/or a venous pressure meter for measuring a venous pressure in the venous blood line, wherein the arterial pressure meter and/or the venous pressure meter are configured to determine at least one pressure measurement value, an alarm output device to output an alarm based on the at least one pressure measurement value, in an alarm event, and a control device for controlling or regulating the blood pump;

providing an alarm criterion memory for storing a predetermined alarm criterion which defines an alarm event;

providing a reference data memory which comprises at least one data set which contains one or more reference pressure profiles or reference pressure values or reference pressure ranges, wherein providing the reference data memory comprises:

at a beginning of or a distinctive point of a treatment session, controlling the blood pump to convey blood along the arterial blood line at one or more reference conveying rates;

at the beginning of or the distinctive point of the treatment session, measuring the pressure prevailing at the one or more reference conveying rates of the blood pump in the arterial blood line and/or venous blood line via the arterial pressure meter and/or the venous pressure meter while or for determining a reference pressure measurement value; and storing at least one data set in the reference data memory, the data set containing the one or more reference pressure measurement values, or at least one reference pressure profile created therefrom;

measuring a prevailing pressure at an initial conveying rate of the blood pump in the arterial blood line and/or in the venous blood line via the arterial pressure meter and/or the venous pressure meter while determining the at least one pressure measurement value;

assessing the at least one pressure measurement value based on the predetermined alarm criterion stored in the alarm criterion memory while or for determining whether the at least one pressure measurement value meets the alarm criterion and that, therefore, there is an alarm event;

controlling the blood pump in order to convey at the one or more reference conveying rates along the arterial blood line, when the pressure measurement value meets the alarm criterion, wherein the one or more reference conveying rates, or at least one of the one or more reference conveying rates is less than the initial conveying rate;

measuring the arterial pressure in the arterial blood line and/or the venous pressure in the venous blood line, respectively prevailing at the one or more reference conveying rates of the blood pump, using the arterial pressure meter and/or the venous pressure meter while determining at least one assessment pressure measurement value;

evaluating the at least one assessment pressure measurement value based on, or via a comparison with, the data set stored in the reference data memory while determining at least one evaluation result; and outputting an alarm via the alarm output device only in the case that the evaluation result satisfies predetermined requirements for outputting an alarm.

2. The method according to claim 1, further comprising stopping the blood pump if or when the predetermined alarm criterion is met before the blood pump is activated to convey the at least one reference conveying rate.

3. The method according to claim 1, further comprising lowering the conveying rate of the blood pump to one of the at least one reference conveying rates, where the one of the at least one reference conveying rates is below the initial conveying rate.

4. The method according to claim 1, further comprising preventing output of the alarm in the event that the pressure measurement value satisfies the alarm criterion stored in the alarm criterion memory, but the evaluation result does not satisfy the predetermined requirements for outputting an alarm.

5. The method according to claim 1, further comprising controlling the blood pump to again convey at the initial conveying rate or a conveying rate related thereto in the event that the evaluation result does not satisfy the predetermined requirements for outputting an alarm.

6. The method according to claim 1, wherein the reference pressure measurement values are determined for the pressures prevailing in both the arterial blood line and the venous blood line, and whereby the evaluation is carried out using the sum and/or the average value of the pressures prevailing in the arterial blood line and venous blood line, based on a corresponding reference pressure value, or via a comparison with the corresponding reference pressure value, which was obtained when evaluating the pressure prevailing in the arterial blood line and venous blood line.

7. The method according to claim 6, wherein the evaluation is carried out after a statistical evaluation.

8. The method according to claim 6, wherein evaluating the pressure prevailing in the arterial blood line and venous blood line comprises a statistical evaluation the sum and/or the average value.

9. The method according to claim 1, wherein the determined reference pressure measurement values are compared with at least one data set from at least one previous treatment session of a same patient and/or reference pressure values recorded from previous treatment sessions of other patients.

10. The method according to claim 9, wherein the determined reference pressure values are used as reference pressure values for the treatment, provided that the comparison with data sets for or from previous treatment sessions satisfies predetermined criteria.

11. The method according to claim 10, wherein the predetermined criteria comprises expected values or ranges obtained from the data sets.

12. The method according to claim 1, wherein evaluating to achieve the evaluation result comprises forming a difference between the at least one assessment pressure measurement value measured by the pressure meter and the one or more reference pressure values contained in the data set, or the reference pressure profile/profiles created from the reference pressure measurement values.

13. A control device, configured to work in interaction with:

a provided blood treatment apparatus, which is connected to a blood tubing set which has an arterial blood line and a venous blood line, wherein the blood treatment apparatus comprises:

a blood pump for extracorporeally conveying blood along the arterial blood line, an arterial pressure meter for measuring an arterial pressure in the arterial blood line and/or a venous pressure meter for measuring a venous pressure in the venous blood line, wherein the arterial pressure meter and/or the venous pressure meter are configured to determine at least one pressure measurement value, an alarm output device for outputting an alarm based on the at least one pressure measurement value in the event of an alarm, and the control device to control or regulate the blood pump;

an alarm criterion memory for storing a predetermined alarm criterion which defines an alarm event;

a reference data memory which comprises at least one data set which contains one or more reference pressure profiles or reference pressure values or reference pressure ranges;

in order to carry out or initiate the method of claim 1.

14. A blood treatment apparatus, comprising:

a blood pump for extracorporeally conveying blood along the arterial blood line, and an arterial pressure meter for measuring an arterial pressure in the arterial blood line and/or a venous pressure meter for measuring a venous pressure in the venous blood line, wherein the arterial pressure meter and/or the venous pressure meter are configured to determine at least one pressure measurement value; and wherein the blood treatment apparatus further comprises or is in signal communication with:

an alarm output device for outputting an alarm based on the at least one pressure measurement value in the event of an alarm;

an alarm criterion memory for storing a predetermined alarm criterion which defines an alarm event;

a reference data memory which comprises at least one data set which contains one or more reference pressure profiles or reference pressure values; and a control device according to claim 13.

15. The blood treatment apparatus according to claim 14, designed as a blood purification apparatus or dialysis apparatus, for hemodialysis, hemofiltration, or hemodiafiltration, or as a plasmapheresis apparatus.

16. A digital storage medium in the form of a floppy disk, CD or DVD or EPROM, with electronically readable control signals, configured to configure a control device into a control device according to claim 13.

17. A computer program product with a program code stored on a machine-readable carrier in order to configure a control device into a control device according to claim 13.

* * * * *